US008187997B2

(12) United States Patent  (10) Patent No.: US 8,187,997 B2
King et al.  (45) Date of Patent: *May 29, 2012

(54) LOW METAL LOADED, CATALYST COMPOSITIONS INCLUDING ACIDIC MIXED METAL OXIDE AS SUPPORT

(75) Inventors: Stephen W. King, League City, TX (US); Stefan K Mierau, South Charleston, WV (US)

(73) Assignee: Union Carbide Chemicals & Technology LLC, Midland, MI (US)

( * ) Notice: Subject to any disclaimer, the term of this patent is extended or adjusted under 35 U.S.C. 154(b) by 13 days.

This patent is subject to a terminal disclaimer.

(21) Appl. No.: 12/587,351

(22) Filed: Oct. 6, 2009

(65) Prior Publication Data

US 2010/0087682 A1 Apr. 8, 2010

Related U.S. Application Data

(60) Provisional application No. 61/195,455, filed on Oct. 6, 2008.

(51) Int. Cl.
  *B01J 23/00* (2006.01)
  *B01J 21/00* (2006.01)
  *B01J 20/00* (2006.01)

(52) U.S. Cl. ........ 502/335; 502/207; 502/241; 502/259; 502/263; 502/303; 502/304; 502/314; 502/315; 502/327; 502/328; 502/332; 502/337; 502/341; 502/351; 502/355; 502/415; 502/439

(58) Field of Classification Search .................. 502/241, 502/242, 258, 259, 263, 327, 332, 335, 337, 502/355, 415, 439, 207, 303, 304, 314, 315, 502/328, 341, 351
See application file for complete search history.

(56) References Cited

U.S. PATENT DOCUMENTS

| | | | |
|---|---|---|---|
| 2,861,995 A | 11/1958 | Mackenzie | |
| 3,110,732 A | 11/1963 | Speranza et al. | |
| 3,658,692 A * | 4/1972 | Gilbert et al. | 208/89 |
| 3,847,754 A | 11/1974 | Oliver | |
| 4,073,750 A * | 2/1978 | Yates et al. | 502/259 |
| 4,111,840 A | 9/1978 | Best | |
| 4,123,462 A | 10/1978 | Best | |
| 4,209,424 A | 6/1980 | LeGoff et al. | |
| 4,264,776 A | 4/1981 | Hershman et al. | |
| 4,328,370 A | 5/1982 | Fazio | |
| 4,400,539 A | 8/1983 | Gibson et al. | |
| 4,404,405 A | 9/1983 | Winters | |
| 4,510,263 A | 4/1985 | Pereira et al. | |
| 4,552,961 A | 11/1985 | Herdle | |
| 4,568,746 A | 2/1986 | Cowherd, III | |
| 4,584,405 A | 4/1986 | Vanderpool | |
| 4,602,091 A | 7/1986 | Brennan | |
| 4,708,945 A | 11/1987 | Murrell et al. | |
| 4,729,981 A * | 3/1988 | Kobylinski et al. | 502/259 |
| 4,801,573 A * | 1/1989 | Eri et al. | 502/302 |
| 4,806,517 A | 2/1989 | Vanderpool et al. | |
| 4,845,296 A | 7/1989 | Ahmed et al. | |
| 4,870,044 A * | 9/1989 | Kukes et al. | 502/220 |
| 4,883,826 A | 11/1989 | Marugg et al. | |
| 4,888,316 A * | 12/1989 | Gardner et al. | 502/20 |
| 4,906,782 A | 3/1990 | Hara et al. | |
| 4,922,024 A | 5/1990 | Bowman et al. | |
| 4,927,931 A | 5/1990 | Molzahn et al. | |
| 4,983,735 A | 1/1991 | Hartwell et al. | |
| 5,030,740 A | 7/1991 | Bowman et al. | |
| 5,073,635 A | 12/1991 | Bowman et al. | |
| 5,120,815 A | 6/1992 | Marugg et al. | |
| 5,166,442 A | 11/1992 | Hartwell | |
| 5,225,599 A | 7/1993 | King et al. | |
| 5,225,600 A | 7/1993 | King et al. | |
| 5,248,827 A | 9/1993 | Hara et al. | |
| 5,256,786 A | 10/1993 | Bowman et al. | |
| 5,288,909 A | 2/1994 | Hartwell et al. | |
| 5,321,160 A | 6/1994 | Hironaka et al. | |
| 5,352,835 A * | 10/1994 | Dai et al. | 564/480 |
| 5,410,087 A | 4/1995 | Hartwell | |
| H1447 H * | 6/1995 | Linton | 428/404 |
| 5,455,352 A | 10/1995 | Huellmann et al. | |
| 5,552,363 A * | 9/1996 | Pannell et al. | 502/337 |

(Continued)

FOREIGN PATENT DOCUMENTS

EP 0075940 4/1983

(Continued)

OTHER PUBLICATIONS

PCT International Search Report for PCT/US2009/005469, pp. 1-5 (2010). PCT International Search Report for PCT/US2009/005473, pp. 1-4 (2010).
PCT International Search Report for PCT/US2009/005476, pp. 1-4 (2010).
PCT International Search Report for PCT/US2009/005472, pp. 1-4 (2010).
PCT International Search Report for PCT/US2009/005480, pp. 1-5 (2010).
PCT International Search Report for PCT/US2009/005471, pp. 1-4 (2010).
PCT International Search Report for PCT/US2009/005477, pp. 1-6 (2010).
PCT International Search Report for PCT/US2009/005470, pp. 1-4 (2010).

(Continued)

*Primary Examiner* — Cam N. Nguyen
(74) *Attorney, Agent, or Firm* — Kagan Binder, PLLC

(57) ABSTRACT

The invention provides a catalyst composition composed of a support portion and a catalyst portion. The support portion includes an acidic mixed metal oxide including a transitional alumina and a second metal oxide. The transitional alumina can comprise delta or theta alumina, in combination with other transitional phases, or an alpha or gamma alumina. The second metal oxide has a weight percentage that is less than the weight percentage of alumina. The catalyst portion is 25 weight percent or less of the catalyst composition and is composed of nickel and rhenium. The catalyst portion includes nickel in an amount in the range of 2 to 20 weight percent, based upon total catalyst composition weight, and there is no boron in the catalyst portion.

16 Claims, No Drawings

U.S. PATENT DOCUMENTS

| | | | |
|---|---|---|---|
| 5,554,793 A | 9/1996 | Hartwell | |
| 5,721,305 A | 2/1998 | Eshuis et al. | |
| 5,750,790 A | 5/1998 | King | |
| 5,851,948 A | 12/1998 | Chuang et al. | |
| 5,935,889 A | 8/1999 | Murrell et al. | |
| 6,117,814 A * | 9/2000 | Plecha et al. | 502/325 |
| 6,124,367 A * | 9/2000 | Plecha et al. | 518/715 |
| 6,169,207 B1 | 1/2001 | Tsuneki et al. | |
| 6,222,008 B1 | 4/2001 | Gelles | |
| 6,235,677 B1 * | 5/2001 | Manzer et al. | 502/232 |
| 6,306,795 B1 * | 10/2001 | Ryan et al. | 502/346 |
| 6,465,530 B2 * | 10/2002 | Roy-Auberger et al. | 518/715 |
| 6,469,214 B2 | 10/2002 | Melder et al. | |
| 6,534,441 B1 * | 3/2003 | Bartley et al. | 502/337 |
| 6,576,796 B1 | 6/2003 | Funke | |
| 6,703,343 B2 * | 3/2004 | Park | 502/355 |
| 6,977,273 B2 * | 12/2005 | Roy-Auberger et al. | 518/715 |
| 7,045,485 B2 | 5/2006 | Kelkar et al. | |
| 7,053,246 B2 | 5/2006 | Gerlach et al. | |
| 7,053,247 B2 | 5/2006 | Lif et al. | |
| 7,056,857 B2 * | 6/2006 | Srinivasan et al. | 502/327 |
| 7,067,455 B2 * | 6/2006 | Chen et al. | 502/325 |
| 7,256,154 B2 * | 8/2007 | Moon et al. | 502/300 |
| 7,323,100 B2 * | 1/2008 | Espinoza et al. | 208/111.3 |
| 7,341,976 B2 * | 3/2008 | Espinoza et al. | 502/327 |
| 7,348,293 B2 * | 3/2008 | Timken | 502/327 |
| 7,393,978 B2 | 7/2008 | Frauenkron et al. | |
| 7,541,310 B2 * | 6/2009 | Espinoza et al. | 502/326 |
| 7,595,276 B2 * | 9/2009 | Kodama et al. | 502/244 |
| 7,745,369 B2 * | 6/2010 | Bhan et al. | 502/246 |
| 7,769,619 B1 * | 8/2010 | Krysinski et al. | 705/7.13 |
| 7,824,656 B2 * | 11/2010 | Idem et al. | 423/651 |
| 7,981,836 B2 | 7/2011 | Kanazirev et al. | |
| 2003/0013873 A1 | 1/2003 | Neumann et al. | |
| 2005/0095189 A1 | 5/2005 | Brey et al. | |
| 2006/0030726 A1 | 2/2006 | Telschow | |
| 2007/0100144 A1 | 5/2007 | Frauenkron et al. | |
| 2008/0003131 A1 | 1/2008 | Bauer et al. | |
| 2010/0056366 A1 * | 3/2010 | Lee | 502/300 |
| 2010/0087681 A1 | 4/2010 | Petraitis et al. | |
| 2010/0087683 A1 | 4/2010 | Cook et al. | |
| 2010/0087684 A1 | 4/2010 | Do et al. | |
| 2010/0087685 A1 | 4/2010 | King et al. | |
| 2010/0094007 A1 | 4/2010 | King et al. | |
| 2010/0094008 A1 | 4/2010 | King et al. | |
| 2010/0137642 A1 | 6/2010 | King et al. | |

FOREIGN PATENT DOCUMENTS

| | | |
|---|---|---|
| EP | 0163253 | 12/1985 |
| EP | 0197611 | 10/1986 |
| EP | 0197612 | 10/1986 |
| EP | 0254335 | 1/1988 |
| EP | 0284398 | 9/1988 |
| EP | 0526851 | 2/1993 |
| EP | 0737669 | 10/1996 |
| EP | 1211238 | 6/2002 |
| EP | 1249440 | 10/2002 |
| EP | 1270543 | 1/2003 |
| GB | 1508460 | 4/1978 |
| IL | 57019 | 9/1983 |
| RU | 2186761 | 8/2002 |
| RU | 2226188 | 3/2004 |
| RU | 2226189 | 3/2004 |
| WO | 99/24389 | 5/1999 |
| WO | 01/44150 | 6/2001 |
| WO | 01/66247 | 9/2001 |
| WO | 01/98243 | 12/2001 |
| WO | 03/010125 | 2/2003 |
| WO | 2005/012223 | 2/2005 |
| WO | 2005/014523 | 2/2005 |
| WO | 2005/061430 | 7/2005 |
| WO | 2006/053342 | 5/2006 |
| WO | 2006/060206 | 6/2006 |
| WO | 2006/114417 | 11/2006 |
| WO | 2007/093514 | 8/2007 |
| WO | 2008/104582 | 9/2008 |
| WO | 2009/083580 | 7/2009 |

OTHER PUBLICATIONS

Kiebich et al., Abstract, "Solvothermal synthesis of [C6H17N3] Sb10S16: A new thioantimonate(III) with an in-situ formed organic amine cation" (2005).

Komiyama et al., "Concentration Profiles in Impregnation of Porous Catalysts: Nickel on Alumina", Journal of Catalysis, vol. 63, School of Chemical Engineering, Cornell University, and Chevron Research Company, pp. 35-52 (1979).

Lewi, Abstract, Database Beilstein (online), Beilstein Institute for Organic Chemistry, Doklady Akademii Nauk SSSR, vol. 78, pp. 725-727 (1951).

Reichle, "Reactions of Aliphatic α-ω-Diamines in H$^+$-Pentasils", Journal of Catalysis, vol. 144, Union Carbide Chemicals and Plastics Company, Inc., Specialty Chemicals Division, pp. 556-568 (1993).

Tanabe et al., "A New Hypothesis Regarding the Surface Acidity of Binary Metal Oxides", Bulletin of the Chemical Society of Japan, vol. 47, Department of Chemistry, Faculty of Science, Hokkaido University, pp. 1064-1066 (1974).

Zagidullin, Abstract, "Simultaneous manufacture of acyclic and cyclic di- and polyethylenepolyamines", Khimicheskaya Promyshlennost, (1987).

* cited by examiner

LOW METAL LOADED, CATALYST COMPOSITIONS INCLUDING ACIDIC MIXED METAL OXIDE AS SUPPORT

CROSS-REFERENCE TO RELATED APPLICATIONS

This application claims benefit from U.S. Provisional patent application having Ser. No. 61/195,455 (filed on Oct. 6, 2008) and entitled LOW METAL CATALYST COMPOSITIONS INCLUDING ACIDIC MIXED METAL OXIDE AS SUPPORT, the disclosure of which is incorporated herein by reference.

FIELD

The invention relates to catalyst compositions that include low levels of metals. More particularly, the invention relates to nickel-rhenium catalysts on an acidic mixed metal oxide support. The acidic mixed metal oxide support includes transitional alumina. The inventive catalysts can be used in transamination reactions to produce ethyleneamine compositions having lower levels of cyclic components.

BACKGROUND

Linear ethyleneamines are known for their many uses in industry. For example, ethylenediamine (EDA) (1,2-diaminoethane) is a strongly basic amine in the form of a colorless liquid having an ammonia-like odor. EDA is a widely used building block in chemical synthesis, with approximately 500,000,000 kg being produced in 1998. EDA is used in large quantities for production of many industrial chemicals, such as bleach activators, fungicides, chelating agents, plastic lubricants, textile resins, polyamide resins, and fuel additives. Diethylenetriamine (DETA) can be used primarily as an intermediate to manufacture wet-strength paper resins, chelating agents, ion exchange resins, ore processing aids, textile softeners, fuel additives, and corrosion inhibitors. Triethylenetetramine (TETA) has such major applications as epoxy curing agents, as well as the production of polyamides and oil and fuel additives.

It is recognized that linear polyalkylene polyamines (such as EDA, DETA and TETA) do not have the same industrial uses and demands as cyclic polyalkyleneamines such as piperazine (PIP). As such, it can be desirable to develop a process with sufficient selectivity in forming a linear polyalkylene polyamine to produce an amine composition with a relatively high ratio of a desired linear polyamine (e.g., DETA) to PIP.

One approach in producing linear ethyleneamines is reductive amination. Reductive amination (also known as reductive alkylation) involves reacting an amine or ammonia with a carbon-containing material. Reductive amination involves the conversion of a carbonyl group (typically a ketone or an aldehyde) to an amine. A classic named reaction is the Mignonac Reaction (1921) involving reaction of a ketone with ammonia over a nickel catalyst, for example, in a synthesis of alpha-phenylethylamine starting from acetophenone.

Reductive amination produces a variety of products, some of which have greater economic value than others, depending upon current market requirements. For example, the reductive amination of monoethanolamine (MEA) produces lower molecular weight linear ethyleneamines, such as EDA, aminoethylethanolamine (AEEA), and DETA. A minor amount of higher linear ethyleneamines, for example TETA and tetraethylenepentaamine (TEPA) are also formed. In addition, cyclic ethyleneamines, such as PIP, hydroxyethylpiperazine (HEP), and aminoethylpiperazine (AEP) are also formed. Cyclic ethyleneamines tend to be less valuable than acyclic ethyleneamines. Accordingly, for maximum economic benefits the catalyst compositions used in commercial reductive amination processes should be selective to the desired mixture of amine products, in addition to being highly active.

It is appreciated in reductive amination art that reductive amination catalysts must first be reduced before effecting the reaction, and then hydrogen gas employed during the course of the reaction in order to maintain catalytic activity and selectivity. During the reaction, reductive amination typically requires addition of ammonia.

One drawback relating to the catalysts and processes that have been described for reductive amination to produce linear polyamines is that they do not typically provide high selectivity to DETA. In these processes, as MEA conversions are increased to produce more DETA, PIP production becomes a significant problem. PIP can be formed from ring closure of DETA or AEEA. Catalysts that are promoted with precious metals are known to show improved activity and selectivity for the reductive amination of MEA to EDA; however, high levels of DETA in the product mix result in concurrent high levels of PIP. As a result, there is still a need for improved catalysts which give high EDA and DETA selectivities while minimizing the amount of PIP formed in the product mixture.

The reductive amination of lower aliphatic alkane derivatives, i.e., diols such as ethylene glycol and alkanolamines such as MEA, is a commercially important family of processes. A variety of catalyst compositions for this purpose is found in the literature and is used commercially. Many of these catalyst compositions are based on nickel/rhenium mixtures (such as nickel/rhenium/boron catalyst compositions and the like) deposited on a support material.

As an alternative to reductive amination, linear polyamines can be prepared by transamination. Transamination is a transfer of an amino group from one chemical compound to another, or the transposition of an amino group within a chemical compound.

Many of the catalysts disclosed for transamination are high metal loaded catalysts. Specifically, Raney nickel catalysts have been employed. These catalysts typically have small particle sizes, which makes their use in fixed bed processes difficult. To address difficulties with small particle sizes, more recent approaches have involved associating the catalytic metals with a support. However, such supported catalysts have typically included very large catalytic metal loading, and such high catalytic metal loading can create its own drawbacks. For example, U.S. Pat. No. 7,053,247 (Lif et al.) describes particulate catalysts containing 26 to 65% by weight of nickel on an oxide carrier. Catalyst compositions including such high levels of catalytic metals can be pyrophoric, more expensive, and do not appear to offer high selectivities for desirable transamination products (e.g., DETA).

Transamination reactions are typically performed at lower temperatures than reductive amination. A general problem in transamination processes of EDA to DETA and higher polyethylenepolyamines is the fact that at moderate temperatures and pressures, these processes can result in too high a proportion of cyclic ethyleneamine compounds, such as PIP, which requires that the EDA conversion be kept low.

SUMMARY

In accordance with aspects of the invention, catalyst compositions useful for transamination of amine-containing solutions are provided. Advantageously, the catalyst compositions can allow for the manufacture of desirable products such as EDA and DETA without generating large amounts of cyclic products such as PIP and AEP. It has been found that catalyst compositions having acidic mixed metal oxide supports in accordance with inventive principles, can provide improved selectivity in transamination reactions. Such improved selectivity can be described as a preference for linear (acyclic) polyamines over cyclic polyamines. In some aspects, the inventive catalyst compositions can also provide improved activity in transamination reactions. For example, in some embodiments, inventive catalyst compositions can be utilized at a lower reaction temperature, where activity of the catalyst can be preserved. Moreover, the inventive catalyst compositions can include a lower metal loading, which can reduce costs.

Generally speaking, the invention provides a catalyst composition comprising a support portion comprising an acidic mixed metal oxide that includes a transitional alumina and a second metal oxide; and a catalyst portion comprising nickel and rhenium, and optionally a promoter. Regarding the support portion, the transitional alumina can comprise delta or theta alumina, alone or in combination with another transitional phase, an alpha alumina, and/or gamma alumina. The second metal oxide has a weight percentage that is less than the weight percentage of alumina. In some aspects, the support portion comprises at least 50 weight percent transitional phase alumina.

Regarding the catalyst portion, the catalyst portion is 25 weight percent or less of the catalyst composition, the catalyst portion comprises nickel in an amount in the range of 2 to 20 weight percent, based upon total catalyst composition weight, and there is no boron in the catalyst portion.

The second metal oxide can comprise at least one element selected from Group IIA, IIIA, IVA, VA, VIA, IIB, IIIB, IVB, VB, VIB, VIIB and a rare earth element of the Periodic Table. In some embodiments, the second metal oxide is selected from silicon, lanthanum, magnesium, zirconium, boron, titanium, niobium, tungsten and cerium. In some illustrative embodiments, the second metal oxide comprises silicon.

In some aspects, the support portion can comprise at least 50 weight percent transitional alumina, or at least 90 weight percent transitional alumina. When present, alpha alumina and/or gamma alumina can be included in an amount less than 50 weight, based upon the weight of the alumina support portion. As discussed herein, the amount of the various phases of alumina can be selected to provide a support portion having a desired surface area, such as in the range of about 10 m²/g to about 200 m²/g.

In some aspects of the invention, the second metal oxide can be present in the support portion in an amount in the range of 5 weight percent to 50 weight percent, based upon the weight of the support portion. In illustrative embodiments, the support portion comprises the second metal oxide in an amount in the range of 5 weight percent to 35 weight percent, based upon the weight of the support portion.

The support portion of the catalyst composition can be provided with a desired surface area. In some embodiments, the support portion has a surface area in the range of about 10 m²/g to about 200 m²/g, or in the range of about 40 m²/g to about 180 m²/g, or in the range of about 80 m²/g to about 180 m²/g. Further, the support portion can be provided with a morphology that minimizes as much as possible mass transfer resistance. In some embodiments, the catalyst composition can be provided with a morphology that reduces or minimizes mass transfer resistance.

In accordance with inventive concepts, the catalyst portion can make up 25 weight percent or less of the catalyst composition. In further embodiments, the catalyst portion is in the range of 3 weight percent to 20 weight percent of the catalyst composition, or in the range of 5 weight percent to 10 weight percent of the catalyst composition.

The inventive catalyst compositions comprise nickel and rhenium as catalytic metals. In some aspects, the nickel and rhenium are present in the catalyst portion in a weight ratio in the range of 3:1 to 14:1.

Optionally, the catalyst composition can further comprise one or more selectivity promoters to enhance selectivity of the catalyst composition. When present, the selectivity promoter can comprise at least one element selected from Group IA, Group IIA, Group IIIA, except for boron, Group IVA, Group VA, Group VIA, Group VIIA, Group VIIIA, Group IB, Group IIB, and Group IVB of the Periodic Table. The selectivity promoter can be present at a promoter/nickel weight ratio of 0 to 0.5.

In another aspect, the catalyst composition of the invention can be used in an amination process. The method includes a step of contacting the catalyst composition of the invention to promote amination of a reactant to provide an aminated product. In some cases the amination process is a transamination process. In particular, the catalyst composition can be used in a method to promote the transamination of EDA to DETA.

The invention also contemplates methods of making catalyst compositions that include a support portion comprising an acidic mixed metal oxide comprising a transitional alumina and a second metal oxide; and a catalyst portion comprising nickel and rhenium.

Surprisingly, the catalyst composition of the invention showed high activity and selectivity for the transamination of EDA to DETA. The catalyst composition of the invention was active at moderate temperatures and pressures, and provided good selectivity to the desired product (DETA) while minimizing unwanted cyclic products, including piperazine and aminoethylpiperazine. In addition, transamination reactions involving the catalyst composition can be performed using very low or no hydrogen as a cofeed. Further, various amines can be fed to the transamination reaction to provide a variety of ethyleneamine mixtures as products. The inventive catalyst compositions can thus provide flexibility in terms of reaction conditions and range of products produced.

The various aspects of the invention will now be described in more detail.

DETAILED DESCRIPTION

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention. The invention is intended to cover all alternatives, modifications, and equivalents that may be included within the scope of the present invention as defined by the claims.

Throughout the specification and claims all percentages used herein are in weight percentages, and are based upon the total weight of the catalyst composition, unless otherwise indicated.

Generally, the invention is directed to catalyst compositions useful in transamination of amine-containing solutions. Catalyst compositions in accordance with inventive principles include those prepared by incorporating at least two catalytically effective transamination metals (nickel and rhenium) on an acidic mixed metal oxide support. The acidic mixed metal oxide support comprises transitional alumina (aluminum oxide ($Al_2O_3$)). Such transamination catalyst compositions can provide a higher ratio of linear (acyclic) to cyclic products when compared to similar catalysts that do not contain a transitional alumina-based acidic mixed metal oxide support.

As discussed herein, the catalyst compositions in accordance with inventive aspects can be utilized to provide the desired linear ethyleneamines at high reactant conversion. In addition to providing high conversion, the inventive catalyst compositions can provide high selectivity for desired linear products.

Features of the catalyst compositions will now be described in more detail.

In some aspects, the invention provides a catalyst composition for transamination of amine-containing solutions, the catalyst composition comprising a support portion and a catalyst portion. According to the inventive aspects, the support portion can comprise an acidic mixed metal oxide. The acidic mixed metal oxide can comprise a transitional alumina and a second metal oxide. In some aspects of the invention, the transitional alumina comprises at least 50 weight percent of the support portion.

Transitional aluminas, or activated aluminas, are described in the *Encyclopedia of Chemical Technology, Volume* 2, *5th Edition*, Kirk-Othmer (1992, page 221 et seq.) as a series of partially hydroxylated aluminum oxides (excluding alpha aluminas which are anhydrous in nature). In general, as a hydrous alumina precursor is heated, hydroxyl groups are driven off, leaving a porous solid structure. As the activation temperature increases through the transitional phases, the crystal structures become more ordered, thus allowing for identification of transitional aluminas by x-ray diffraction (hereafter "XRD"). The sequences of transition are affected not only by the starting materials, but also by the coarseness of crystallinity, heating rates, and impurities. The following transitions are generally accepted as the transitions when the starting material is coarse gibbsite in air:

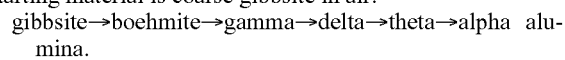
gibbsite→boehmite→gamma→delta→theta→alpha alumina.

Of the transitional aluminas described above, the delta and theta phases can be particularly useful as a support portion of a catalyst composition in accordance with the invention. Other useful aluminas include mixtures of transitional aluminas and aluminas such as gamma/theta, gamma/delta, delta/theta, theta/alpha phases, or combinations thereof.

Transitional alumina carriers may be characterized using an X-ray diffractometer by methods known in the art. The following Table 1 lists the accepted 2-theta values for the aluminas, as supplied by the Joint Committee on Powder Diffraction Standards International Center for X-Ray Diffraction:

($\alpha$-alumina) as a combination with a transitional alumina. In other embodiments, alumina can be employed in its most amorphous state, gamma-alumina, in combination with a transitional alumina. However, in either of these cases, the transitional forms of alumina are predominant in the alumina mixture.

As noted above, alpha alumina is not considered a transitional phase of alumina. Rather, alpha alumina is the most thermodynamically stable form of alumina, and once formed, this phase is irreversible. Typically, then, alpha alumina is not present in a significant amount in the support portion of the inventive catalyst compositions. Although the crystallinity of alpha alumina is highly distinctive when compared to the transitional aluminas, in mixed phases that contain small amounts of alpha alumina, the amount of alpha alumina present is not easily quantified. However, due to the extremely low surface areas of alpha aluminas, useful mixed phases containing alpha alumina can be determined by those which fall within the surface area ranges described herein.

Similarly, while gamma alumina is not considered a transitional phase of alumina, it may also be present in the support portion. As with alpha alumina, gamma alumina is not typically present in a significant amount in the support portion. Useful mixed phases containing gamma alumina can be determined by those which fall within the surface area ranges described elsewhere herein.

Generally speaking, transitional aluminas are considered to be intermediate surface area supports. In accordance with the invention, support portions comprising transitional alumina can have surface areas in the range of about 10 $m^2/g$ to about 200 $m^2/g$, or about 40 $m^2/g$ to about 180 $m^2/g$, or about 80 $m^2/g$ to about 180 $m^2/g$.

As noted above, transitional aluminas can be obtained by heat-treating transitional alumina precursor materials such as gibbsite, boehmite, or bayerite to the desired phase transformation temperature. Processing can involve heat treatment of a transitional alumina precursor into transitional alumina, in the form of delta or theta alumina, or combinations thereof. Other techniques rely upon direct synthesis via a wet chemical processing, such as through hydrolysis of aluminum alkoxide.

In another embodiment, transitional alumina material can be formed through a seeded processing pathway, such as that described in PCT/US2005/042048 ("Transitional Alumina Particulate Materials Having Controlled Morphology and Processing for Forming Same," Bauer et al.) and U.S. Patent Publication No. 2008/0003131 A1 ("Transitional Alumina Particulate Materials Having Controlled Morphology and Processing for Forming Same," Bauer et al.). The transitional alumina can be present as a mass of particulate material, composed of particles that may be fully dispersed, partially

TABLE 1

| Aluminas | | | | | | | |
|---|---|---|---|---|---|---|---|
| gamma | 19.58 | 31.94 | 37.60 | 39.49 | 45.79 | 60.76 | 66.76 |
| delta | 17.65 | 19.49 | 21.82 | 31.14 | 32.78 | 34.74 | 36.96 | 39.49 |
| | 45.55 | 46.54 | 47.57 | 50.67 | 60.03 | 61.35 | 62.26 | 64.18 |
| | 66.76 | 67.31 | 73.33 | 75.37 | | | | |
| theta | 15.5 | 16.25 | 19.54 | 31.509 | 32.778 | 34.939 | 36.743 | 38.871 |
| | 39.911 | 44.856 | 46.4242 | 47.5849 | 50.6803 | 51.3931 | 52.6308 | 54.5575 |
| | 56.7218 | 58.7033 | 61.2553 | 62.3387 | 64.0501 | 65.3714 | 67.4008 | |
| alpha | 25.5 | 35.4 | 38.0 | 43.6 | 52.8 | 57.6 | 63.05 | 66.7 |
| | 68.4 | | | | | | | |

In some aspects of the invention, alumina can be employed in its hardest and most stable allotropic state, alpha-alumina agglomerated, or fully agglomerate. In the dry form, the particulate material may be in the form of a powder. This process typically includes providing a boehmite precursor and boehmite seeds in a suspension, sol or slurry. The suspension, sol or slurry can be heated treated (such as by hydrothermal treatment) to convert the boehmite precursor into boehmite particulate material formed of particles or crystallites. Heat treatment is then carried out to the boehmite particulate material to effect polymorphic transformation into transitional alumina.

The transitional alumina precursor can be heat treated by calcination at a temperature sufficient to cause transformation into a transitional phase alumina, or a combination of transitional phases. Typically, calcination or heat treatment can be carried out at a temperature greater than about 250° C., but lower than about 1100° C. At temperatures less than 250° C., transformation into the lowest temperature form of transitional alumina, gamma alumina, typically will not take place. At temperatures greater than 1100° C., typically the precursor will transform into the alpha phase. According to certain embodiments, calcination is carried out at a temperature greater than 400° C., such as not less than about 450° C. The maximum calcination temperature may be less than about 1050° C. or 1100° C., these upper temperatures usually resulting in a substantial proportion of theta phase alumina, the highest temperature form of transitional alumina.

When it is desired to form a substantial content of delta alumina, the transitional alumina precursor can be calcined at a temperature lower than about 950° C., such as within a range of about 750° C. to about 950° C. In some embodiments, calcination can be performed at temperatures above about 750° C., or above about 775° C., or above about 800° C., to avoid transformation into a predominant gamma phase alumina.

Calcination of the transitional alumina precursor can be carried out in various environments including controlled gas and pressure environments. Because calcination is generally carried out to effect phase changes in the precursor material and not chemical reaction, and since the resulting material is predominantly an oxide, specialized gaseous and pressure environments need not be implemented in most cases.

Typically, calcination can be carried out for a controlled time period to effect repeatable and reliable transformation from batch to batch. Calcination times typically range from about 0.5 minutes to about 60 minutes, typically about 1 minute to about 15 minutes.

Generally, as a result of calcination, the alumina material used to form the support portion is predominantly (more than 50 weight percent) transitional alumina. The precise makeup of transitional alumina phases may vary according to different embodiments, such as a blend of transitional phases. In some embodiments, a predominant amount of a particular transitional phase can be present, such as at least about 50 weight percent, or at least about 60 weight percent, or at least about 70 weight percent, or at least about 80 weight percent, of a desired transitional phase. In further embodiments, the transitional alumina can comprise essentially a single phase of transitional alumina (e.g., at least 95 weight percent, or at least about 98 weight percent, or even up to about 100 weight percent of a single phase of transitional alumina). As discussed herein, the particular phase(s) of transitional alumina can be determined by XRD.

Illustrative aluminas suitable for inclusion in the support portion include delta, theta, gamma/delta, gamma/theta, delta/theta, and theta/alpha phases. In some embodiments, when alpha alumina is included in the alumina support portion, it can be present in an amount that is about 49 weight percent or less. In some embodiments, when gamma alumina is included in the alumina support portion, it can be present in an amount that is about 49 weight percent or less. In still further embodiments, the support can include one or more of the following additional alumina transitional phases: kappa, eta, rho, chi alumina, and combinations thereof.

In accordance with inventive aspects, the alumina is combined with a second metal oxide to provide an acidic mixed metal oxide. Illustrative second metal oxides include oxides that, when combined with the alumina, can provide sufficient surface acidity to serve as a support portion for the catalyst composition. Some binary metal oxides are known to have surface acidity and have been used as solid acid catalysts, such as silica-alumina and alumina-boron oxide. Additional mixed metal oxides that may generate surface acidity can be determined using the hypothesis described by Tanabe et al. (*A New Hypothesis Regarding the Surface Acidity of Binary Metal Oxides*, Bulletin of the Chemical Society of Japan, 47(5):1064-1066 (1974)).

Useful second metal oxides comprise at least one element selected from Group IIA, IIIA, IVA, VA, VIA, IIB, IIIB, NB, VB, VIB, VIIB and a rare earth element of the Periodic Table. Illustrative second metal oxides in accordance with some embodiments include silicon, lanthanum, magnesium, zirconium, boron, titanium, niobium, tungsten and cerium. In some embodiments, the second metal oxide can comprise silicon.

Acidic mixed metal oxides can be prepared by one skilled in the art. Such known preparation methods include coprecipitation of metal salts, sol-gel techniques, ion exchange, mechanical mixing, and incipient wetness or precipitation on metal oxides.

The inclusion of an acidic mixed metal oxide comprising transitional alumina in the support portion along with the low metal loading can provide improved catalyst compositions. For example, catalyst compositions in accordance with the invention can include surprisingly low (e.g., 25 weight percent or less) concentrations of catalytic metals. Reduction in the amount of catalytic metals required to provide the desired activity and selectivity can provide significantly lower catalyst costs. Surprisingly, the low-metal loaded catalyst compositions of the invention demonstrate high activity and selectivity for the transamination of EDA to DETA. The catalyst is active at moderate temperatures and pressures and can provide good selectivity to the desired product (DETA) while minimizing cyclic products such as PIP and AEP.

The acidic mixed metal oxide support portion can be provided in any convenient morphology. The shape of the support will typically depend upon the shape required by the particular apparatus used to perform the transamination reaction. Catalyst compositions can be made on supports in the form of particles, powders, spheres, extrudates, pellets (cut extrudates), trilobes, quadrilobes, rings and pentarings. In some embodiments, particles can have an elongated morphology, which can be described generally in terms of the particle's aspect ratio. The aspect ratio is the ratio of the longest dimension to the next longest dimension perpendicular to the longest dimension. Alternatively, particles can have a platelet-shape, wherein the particles generally have opposite major surfaces, the opposite major surfaces being generally planar and generally parallel to each other.

Morphology of the support portion can be further described in terms of support portion size, more particularly, average support portion size. Average support portion size can be described as the average longest or length dimension of the support material. Average support portion size can be determined by taking multiple representative samples and physically measuring the support material sizes found in representative samples. Such samples may be taken by various characterization techniques, such as by scanning electron microscopy (SEM). In some aspects, the support portion can be provided in the form of an extrudate. Extrudates ranging in diameter of about 1/8" (3.175 mm) or less can be useful, for example in the range of about 1/32" (0.79375 mm) to about 1/8". Another useful form of the support portion is a trilobe. Trilobes having a diameter of about 1/8" or less can be useful, for example in the range of about 1/16" (1.5875 mm) to about 1/8". Yet another useful support form is a sphere, such as spheres having a diameter of 3 mm or less.

In addition to the shape and average support material size, yet another useful way to characterize morphology of the support portion is to describe the specific surface area of the support portion. The acidic metal oxide complex can be provided with a range of surface areas ($m^2/g$), as measured by the commonly available BET technique. According to embodiments herein, the support portion can have a relatively high specific surface area, generally not less than about 10 $m^2/g$, such as not less than about 40 $m^2/g$, or not less than about 80 $m^2/g$, or not less than about 90 $m^2/g$. Since specific surface area is a function of particle morphology as well as size, generally the specific surface area of embodiments can be less than about 200 $m^2/g$, such as less than about 150 $m^2/g$, or less than about 100 $m^2/g$. In some embodiments, the surface area can be in the range of about 80 $m^2/g$ to about 180

Other useful characteristics of the support portion include pore volume (expressed as Hg intrusion values or $N_2$ values), and water absorption (expressed as a percentage of the dry sample weight). Illustrative pore volume (Hg pore symmetry) ranges are about 0.3 $cm^3/g$ to about 1 $cm^3/g$. The percent water absorption is not narrowly critical since the catalyst portion is less than 25 percent and can be easily incorporated using incipient wetness techniques known to one skilled in the art. Another characteristic of the support is the median pore diameter. Again the median pore diameter is not narrowly critical over the surface area of the invention. Additionally, the pore size distribution may be unimodal or multimodal (e.g., bimodal, trimodal, etc.).

The inventive catalyst compositions comprise the support portion described above, and a catalyst portion that comprises nickel and rhenium. Details of the catalyst portion will now be described in more detail.

Various methods can be carried out for associating/immobilizing the metals of the catalyst portion with the catalyst support. In some modes of practice, the metals of the catalyst portion (nickel and rhenium, used together, or along with one or more other metals) are associated with the support portion by impregnation. Impregnation is particularly suitable for this process, since the lower metal loadings are used.

Although impregnation is one mode of preparing the catalytic support, other methods can be used to associate the catalytic metals with the support portion. For example, the metals can be deposited on the support material by co-precipitation, sol-gel techniques, chemical vapor deposition, or ion exchange. These alternative methods are well known in the art and can be used for the preparation of the catalyst support if desired. In order to describe the process of associating the catalytic metals with the support, steps of an impregnation method will be described.

As a general matter, the process of depositing the catalytic metals can be performed to provide a support with a desired amount of the metals. As used herein, the total amount of the catalytic metals in the compositions is referred to herein as the "catalyst portion," and the amount of the catalyst portion is expressed as a percentage by weight of the catalytic composition. According to the invention, the catalyst portion has an amount of metals of 25 weight percent or less of the total weight of the catalyst composition. Lower amounts of the catalyst portion can be used, such as about 20 weight percent or less of the total weight of the catalyst composition. A catalyst composition that is 10 weight percent of the catalyst composition has 10 g of a catalyst metal, or a combination of catalyst metals, associated with 90 g of the support.

While the invention contemplates inclusion of a catalyst portion having an amount of metals of 25 weight percent, lower amounts of the catalyst portion can be used, such as about 10 weight percent or less of the total weight of the catalyst composition. Generally, the catalyst portion includes enough of the nickel and rhenium to provide a desired catalytic activity when used in an amination process, such as transamination. However, upon review of this disclosure, it will be apparent that lower amounts can be used which provide an economic advantage while still providing desirable catalytic activity and selectivity. For example, in some modes of practice the amount of metals (nickel and rhenium, used together, or along with one or more other metals) in the catalyst portion is in the range of about 3 weight percent to about 20 weight percent of the catalyst composition, or in the range of about 5 weight percent to about 10 weight percent of the catalyst composition. Lower (below 3 weight percent) amounts of the catalyst portion may be used, although it is understood that catalytic activity may be decreased as well. Although lower catalytic activity may be acceptable in some catalytic methods, most others would benefit from higher levels (i.e., above about 3 weight percent).

The catalyst composition includes a catalyst portion wherein boron is not present in the catalyst portion, or, alternatively, used only in very small amounts. For example, in many modes of practice the catalyst composition is prepared without including boron when the catalyst portion is immobilized on the catalyst support. Any boron present in the catalyst portion is desirably less than 1 weight percent, less than 0.5 weight percent, or less than 0.3 weight percent.

In some preparations of the catalyst composition, the catalyst portion includes a mixture of nickel and rhenium in the composition in a predetermined weight ratio. In some cases, the weight ratio of the nickel and rhenium in the composition is in the range of about 3:1 to about 15:1. In some aspects, nickel is present in an amount in the range of about 23 weight percent to about 2 weight percent, and rhenium is present in the composition in the range of about 7 weight percent to about 0.5 weight percent. In some aspects, nickel is present in an amount in the range of about 5 weight percent to about 8.5 weight percent, and rhenium is present in the composition in the range of about 2.5 weight percent to about 1 weight percent. An exemplary catalyst portion includes nickel at about 6.8 weight percent and rhenium at about 1.8 weight percent.

In some aspects, the selectivity of the catalyst composition may be further enhanced by the use of metal promoter. The promoter may be a metal (or oxide) which when incorporated into the catalyst composition further enhances the productivity and/or selectivity in the amination reaction. As an example, metals or metal oxides for use as promoters, in addition to the nickel and rhenium, are compounds containing elements selected from Group IA, Group IIA, Group IIIA, Group IVA, Group VA, Group VIA, Group VIIA, Group VIIIA, Group IB, Group IIB and Group IVB of the Periodic Table (IUPAC format). Exemplary metals include, for example, copper, cobalt, chromium, rhodium, iridium, ruthenium, zinc, palladium, platinum, sodium, calcium, magnesium, strontium, lithium, potassium, barium, cesium, lanthanum, tungsten, iron, silver, titanium, manganese, niobium, aluminum, tin and mixtures of these metals. Some particularly useful metals include magnesium, zinc, niobium, chromium, ruthenium, cobalt, copper, tin and mixtures thereof.

Promoters can be added to the catalyst composition either by co-impregnation with nickel and rhenium or they can be added to the support either before or after incorporation of the nickel and rhenium salts. It should also be understood that the nickel and rhenium need not be added simultaneously with each other or with the promoter; the promoter, nickel and rhenium combination can be added in any sequence. Promoters can be added to the catalyst composition at desirable levels which are generally no higher than the nickel present in the catalyst composition on a weight percent basis. In some embodiments, a promoter/nickel ratio of 0 to about 0.5 can be useful.

In some modes of practice the metals of the catalytic portion are deposited on the support using an incipient wetness technique, often referred to as incipient wetness impregnation (IW or IWI). In this technique an active metal precursor (or combination of active metal precursors) is dissolved in an aqueous or organic solution. The metal-containing solution ("impregnation solution") is added to a catalyst support. Often, the impregnation solution is added in a volume that is the same as the pore volume of the support. Capillary action draws the impregnation solution into the pores of the support. The impregnated support can then be dried and calcined to drive off the volatile liquids of the impregnation solution. This process deposits the catalytic metals on the surface of the support portion.

In some modes of practice, an aqueous solution of a salt of the metal is prepared (the impregnation solution). Since more than one metal is to be immobilized on the support, the impregnation solution can include a mixture of salts of the desired metals. Alternatively, more than one impregnation solution can be prepared. The impregnation solution can be saturated with the metal salts, or the metal salts can be used in amounts less than saturation. The concentration of the metal salts in the impregnation solution can depend on factors such as the desired amount of metal(s) to be deposited on the support, and the solubility of the particular metal salt(s) used in the process.

Organic and inorganic salts of nickel include, but are not limited to, nickel nitrate hexahydrate, nickel formate, nickel acetate tetrahydrate, nickel acetate, nickel chloride, nickel carbonate and the like. A nickel-containing impregnation solution can be prepared containing one or more of these nickel salts. In some modes of practice, nickel nitrate or nickel formate is used to prepare the impregnation solution.

Precursor salts of rhenium include potassium and ammonium salts. Additionally, perrhenic acid may also be used. A rhenium-containing impregnation solution can be prepared containing one or both of these salts.

In many modes of practice, the one or more metals to be deposited on the support are dissolved in a suitable solvent, such as deionized water, for preparation of the impregnation solution.

One or more impregnation solutions can be prepared to provide the types and total amount of metals to be deposited on the support portion. Since a lower amount of metal is associated with the support, the total amount of metal can be deposited in a limited number of applications. For example, the total amount of metal deposited can be applied in one, two, three, or four applications. Although an impregnation solution can be prepared with a high concentration of metal salt (i.e., a minimal amount of water), in some cases the total amount of the impregnation solution to be applied may be more than what the alumina support can hold by absorption. Therefore, in some modes of practice, the impregnation solution is applied to the support in multiple steps, wherein a portion of the impregnation solution about equal to the absorption volume of the support is applied to the support in one application step. Incorporation of additional metal(s) into the support may be further increased by techniques known to those skilled in the art, such as increasing the time the support is in contact with the solution.

The impregnation solution can be applied to the support using various methods. For example, the solution can be applied processes such as drip application, by immersion (e.g., dipping), or by spraying. During application, the support can be agitated by processes such as mixing, tumbling, stirring, or shaking. Mechanical equipment can be used to facilitate agitation. Agitation during the application of the impregnation solution can increase the uniformity of the impregnation solution applied to the support.

After all or a portion of the impregnation solution is applied to the support, the support can be dried. In the drying step, the liquid which solvates the metal salt is volatized and removed from the support. The drying may be accomplished by any technique that sufficiently evaporates the volatile constituents of the impregnation solution. The drying step can comprise a calcination step, as further discussed herein. Multiple drying steps can be performed if the impregnation solution is applied in more than one step. Therefore, an overall process for preparing the catalyst composition can include multiple steps of disposing the application composition, and then drying the impregnated support. The steps of depositing and then drying can be performed until all of the impregnation solution is used.

Typically, the impregnated support is dried at a temperature of above 100° C. The elevated temperature can also be accompanied by a reduced pressure environment to accelerate removal of the liquid from the support. The support can be dried in air or in the presence of an inert gas, such as nitrogen. Drying is carried out for a period of time sufficient for removal of most or all of the liquid of the impregnation solution. In some modes of practice, the step of drying is performed for a period of about one hour or more at elevated temperatures.

The process of preparing the catalytic composition can also involve one or more steps of calcining the support. One or more steps of calcining the support can be performed in the absence of the catalytic metals, and optionally in the presence of the catalytic metals, or both.

In some modes of practice, given the high heat of calcination, drying and removal of the liquid component of the impregnation solution occurs. Therefore, as used herein, calcination of the support meets the requirements of the drying step or steps, which are typically performed following application of the impregnation solution. In addition, calcination can cause conversion of the metal salts into oxides. The choice of a particular calcination temperature can depend on the decomposition temperature of the salts used.

Calcination normally takes place at temperatures below the melting point of the materials used to form the support portion of the catalytic composition. For example, calcination is typically performed in the range of about 200° C. to about 1200° C., and more typically in the range of about 300° C. to about 500° C. A calcination step can take for a period of time in the range of a minute to hours (e.g., two or three or more hours). Calcination can be carried out in the presence of air, or under inert gas.

In some modes of practice calcination is performed after one or more steps of applying the impregnation solution. After all of the impregnation solution has been applied the metal-loaded support can be calcined for a longer period of time to ensure substantial removal of the impregnation solution liquid. For example, in some specific modes of practice, the impregnation solution is applied to the support in two or more steps, with calcination at about 340° C. for about one hour in air performed after each step of applying, with a final calcination at about 340° C. for about one hour in air.

Following metal impregnation and calcination, the catalyst composition can be reduced, converting the metal oxides produced in the calcination step to the reduced metal form. Typically, the metal-containing support is reduced in the presence of hydrogen. The metal-containing support can be contacted with hydrogen gas at a temperature that is about in the same range as that used for calcination. The process of reduction can be carried out from about 30 minutes to about 24 hours, or more.

Following reduction, the catalyst composition can be stabilized with gentle oxidation. Typical stabilizing treatments involve contacting the reduced catalyst composition with oxygen or carbon dioxide. For example, in one mode of practice, the catalyst composition is treated with about 1% $O_2/N_2$. Prior to using in an amination reaction, the catalyst composition can be activated with hydrogen.

After impregnation and drying/calcination (with optional reduction) the catalyst composition can optionally be stored or handled in an inert environment.

In some aspects, the invention relates to methods for making a catalyst composition in a manner that reduces or minimizes mass transfer resistance for the transamination of the amine-containing solution. Various techniques are known in the art to account for mass transfer resistance in supported catalysts. Some illustrative methods for addressing mass transfer resistance include: adjusting the morphology of the catalyst composition, selecting the form of the catalyst composition (e.g., by providing a thin coating of the active catalyst metals on the surface of the support), and/or the selecting the size of the catalyst particles.

Accordingly, in some embodiments, the morphology of the catalyst composition can be controlled to reduce or minimize mass transfer resistance. For example, PCT Publication No. WO 2006/060206 ("Transitional Alumina Particulate Materials Having Controlled Morphology and Processing for Forming Same," Bauer et al.) describes alumina particulate material that contains particles comprising transitional alumina having an aspect ratio of not less than 3:1 and an average particle size of not less than about 110 nm and not greater than 1000 nm. Various shaped particles are described, including needle-shaped particles and platy-shaped particles.

In other embodiments, the catalyst portion is deposited on a porous support portion so that at least the active catalyst metals are provided in a very thin outer layer or "egg shell" structure, so as to minimize mass transfer resistance for the amine-containing solution. This catalyst structure can also lower the active metal requirement for the catalyst composition, and/or maximize contact of the active metals with the amine-containing elements within the reaction solution.

Thus, in accordance with these embodiments, useful catalyst composition diameters can be in the range of about 0.8 mm to about 3.1 mm; surface area can be in the range of about 10 $m^2/g$ to about 200 $m^2/g$; catalytically active metal concentration can be in the range of about 1 weight percent to about 25 weight percent, and the catalyst portion can be provided as a thin outer shell on the support portion.

Methods described in U.S. Pat. No. 5,851,948 can be utilized to create a similar "egg shell" structure for the present inventive catalyst compositions. For example, the catalytic metals comprising the catalyst portion (here, nickel and rhenium) can be added to the support portion as a thin outer layer or shell on the support portion. This small thickness for the catalyst portion can be influenced by the flow characteristics of the nickel and rhenium salts and a suitable carrier liquid solution of an alcohol and water, the porosity and surface area of the support portion, and the diffusion rate of the active metal liquid solution into the porous support portion. The flow characteristics of the nickel and rhenium in the alcohol-water carrier liquid having low surface tension is controlled so as to initially form a "cluster"-type structure of the nickel and rhenium in the carrier liquid on only the outer surface of the support portion. Such "cluster" type structures are formed because of valence differences between ions of the active nickel and rhenium and molecules of the alcohol carrier liquid, and such larger "clusters" effectively impede penetration of the active metal into smaller size pores of the support material. During the subsequent drying, reducing and calcining steps for making the catalyst, the carrier liquid is destroyed and removed so that only the active metals remain in uniformly dispersed sites in the thin outer "egg-shell" structure on the support portion. Suitable alcohol carrier liquids may include ethanol, methanol and isopropanol.

This technique of depositing an active metal such as nickel and/or rhenium in a thin layer or shell on only the outer surface of the support portion advantageously provides a high localized concentration of the active metals on the catalyst outer surface, where it is readily contacted by the amine-containing compounds in the reaction solution. Techniques described in U.S. Pat. No. 5,851,948 (Chuang et al., "Supported Catalyst and Process for Catalytic Oxidation of Volatile Organic Compounds") can be instructive in accordance with these embodiments of the invention.

Catalytic metal can also be deposited on the surface of the support portion according to techniques described by Komiyama et al. ("Concentration Profiles in Impregnation of Porous Catalysts: Nickel on Alumina," J. of Catalysis 63, 35-52 (1980)). Utilizing the principles described by Komiyama et al., radial concentration profiles in the catalyst compositions can be formed by impregnating the support portion with aqueous catalytic metal (e.g., nickel) solutions. In accordance with the present invention, a base can be used with nickel-formate to achieve surface deposition of nickel on alumina supports. More specifically, the pH effect on adsorption has been utilized to achieve surface impregnation of nickel by coimpregnating alumina supports with nickel formate ($Ni(HCOO)_2 \cdot 2H_2O$) and aqueous ammonia. The result was surface deposition of the nickel on the alumina supports. These principles can be further applied to catalyst compositions including more than one catalytic metal (e.g., more than one of cobalt, nickel, and/or copper).

In still further embodiments, internal mass transfer resistance can be controlled by selecting a desirable particle size for the support portion. As discussed in European Patent Application No. EP 1249440 A1 ("Process for Preparing Linear Alkylbenzenes," Wang et al.), both the catalyst particle size and porosity can be adjusted to provide a desired conversion and catalytic stability.

In use, the catalyst composition is added to promote an amination reaction, such as a transamination process. The amount of catalyst composition that is used to promote an amination reaction can be determined based on one or more of the following factors: the type and amount of reactants, the reactor (reaction vessel) configuration, the reaction conditions (such as temperature, time, flow rate, and pressure), the degree of conversion to a desired product(s), and the selectivity desired (i.e., the ratio of the desired product over an undesired product). The catalyst composition is present in the reaction zone in sufficient catalytic amount to enable the desired reaction to occur.

The catalyst composition can be used for promoting a transamination reaction, such as the transamination of a lower aliphatic alkane derivative. In one exemplary mode of practice, the catalyst composition is used for promoting the transamination of ethylenediamine (EDA) to diethylenetriamine (DETA). The general reaction for the process is shown below:

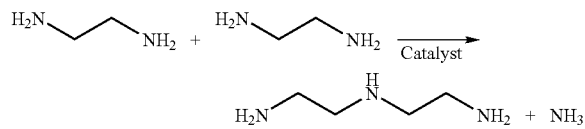

The use of the catalyst composition will now be described with more specificity for the transamination of EDA to DETA. EDA is a colorless liquid with an ammonia-like odor and has molar mass of 60.103 g/mol, a density of 0.899 g/cm$^3$, a melting point of 9° C., a boiling point of 116° C. EDA is miscible in water and soluble in most polar solvents.

The products found in the reaction mixture (i.e., the output of the reaction) include transaminated products, with diethylenetriamine (DETA) being the desired product in many modes of practice. Triethylenetetramine (TETA) may be also be found, which results from the further reaction of DETA with EDA. Higher order polyamines formed in a similar manner may also be present in the reaction product mixture. Piperazine is also a transamination product, which is desirably present in lower amounts in some modes of practice. Aminoethylpiperazine (AEP) is also formed in the reaction mixture. The reaction products may also include unreacted ethylenediamine, ammonia (which is eliminated in the transamination reaction), and hydrogen.

The products in the reaction mixture are normally subjected to a separation step. In the separation step hydrogen and ammonia (the low molecular weight compounds) are separated from unreacted ethylenediamine and the transamination products by fractional distillation. Hydrogen and ethylenediamine are typically returned to the process.

Operating conditions can be chosen to provide a desired rate of conversion, which has been shown to affect the selectivity for the desired product. In particular, conditions are established to provide a certain rate of conversion of EDA, resulting in a desired selectivity for DETA. For purposes of this invention, "EDA conversion" refers to the total weight percentage of reactant (e.g., EDA) lost as a result of reactions. The conversion can vary depending upon factors such as the reactants, catalyst, process conditions, and the like. In many embodiments, the conversion (e.g., of EDA) is at least about 10%, and desirably less than about 50%, and in some modes of practice in the range of about 20% to about 40%. The temperature of reaction can be selected to provide a desired degree of conversion, which is discussed further herein. In some modes of practice the desired conversion of EDA is about 25%.

For purposes of the invention, "selectivity" refers to the weight percentage of converted reactant(s) that form a desired transaminated product, such as DETA. In some modes of practice the percent selectivity to DETA is about greater than 50%, greater than 65%, such as in the range of about 65% to about 75%. Like conversion, selectivity will vary based upon factors including the conversion of the reactant(s), feed reactants, catalyst, process conditions, and the like.

The mixture of reaction products can also be defined in terms of the weight ratio of two products in the mixture. Typically, ratios useful for assessing the quality of the reaction mixture are of a desired product to an undesired product (e.g., DETA/PIP), or desired product to a different desired product (e.g., DETA/TETA). For example, the mixture of reaction products can be described in terms of the weight ratio of DETA to piperazine (DETA/PIP) at an EDA conversion of 25%. In some modes of practice, the catalyst composition of the invention is used in a transamination reaction to provide a DETA/PIP ratio of about 9:1 or greater, about 10:1 or greater, about 11:1 or greater, about 11.5:1 or greater, or about 12.0:1 or greater, such as in the range of about 9:1 to about 13:1, or about 10:1 to about 13:1, or about 11:1 to about 13:1, or about 11.5:1 to about 13:1, or about 12:1 to about 13:1.

The weight ratio of TETA to PIP, may also be useful for determining the selectivity of the reaction. In some modes of practice, the catalyst composition of the invention is used in a transamination reaction to provide a TETA/PIP ratio at an EDA conversion of 25% of about 0.75:1 or greater, about 0.8:1 or greater, or about 0.9:1 or greater, 1:1 or greater, about 1.1:1 or greater, about 1.2:1 or greater, or about 1.3:1 or greater, or about 1.4:1 or greater, such as in the range of about 0.75:1 to about 1.5:1, about 0.8:1 to about 1.5:1, about 0.9:1 to about 1.5:1, or about 1:1 to about 1.5:1.

Using the catalyst composition of the present invention, transamination can be performed using any suitable method and reaction equipment. For example, transamination can be carried out using a continuous process, a semi-continuous process, a batch-wise process, or a combination of these processes. The transamination process using the catalyst composition of the present invention can be carried out in a conventional high-pressure equipment with a heating feature. The equipment can have one or more features which cause movement of the reactants and/or catalysts in the equipment, such as an agitator or pump. Various reactor designs can be used, such as a stirred-tank, fixed-bed, slurry, or fluid-bed reactors. The reactors can be designed for liquid-phase, gas-phase, multi-phase or super-critical conditions.

In some modes of practice, the reactant (e.g., EDA) is provided to the reaction bed that includes the catalyst composition as a stream, the stream having continuous flow. The reactant feed can be upflowing or downflowing. Design features in the reactor that optimize plug flow can also be used. Effluent from the reaction zone is also a stream comprising the unreacted components of the feed stream (such as EDA) and the reaction products (DETA). In some modes of practice, a liquid EDA is established in an upflow direction into the catalyst bed. In some modes of practice, a flow rate is established to provide a space velocity in the range of about 5 gmol/hr/kg catalyst to about 50 gmol/hr/kg catalyst, with an exemplary space velocity of about 15 gmol/hr/kg catalyst.

The transamination reaction can be carried out with little or no hydrogen. However, as an optional component, hydrogen gas can be present during the transamination reaction. In some cases, hydrogen may facilitate the production of the reaction product, and inhibit or reduce poisoning of the catalyst. If desired, hydrogen can be included prior to and/or within the transamination reactor in an amount sufficient to affect catalyst activity and product selectivity. Exemplary amounts of hydrogen include 0.001 to 10.0 mole % based on liquid feed. A source of hydrogen gas can optionally be combined with the ethyleneamines source and fed to the transamination reactor.

Optionally, ammonia can be used affect selectivity by inhibiting undesired reactions.

Generally, reaction temperatures for transamination process fall within the range of about 110° C. to about 180° C., and in desired modes of practice a reaction temperature in the range of about 130° C. to about 160° C. are used. The temperature can be varied throughout the reaction process, and may fluctuate up to about 30%, or up to about 20% of the starting temperature. The temperature of reaction can be selected to provide a desired rate of conversion. In many modes of practice, the temperature is chosen to provide a relatively low rate of conversion.

Typical reaction pressures range from about 200 psig to about 2000 psig, about 400 psig to about 1000, and in some desired modes of practice the pressure is about 600 psig.

The catalyst compositions of the present invention can be used in the methods described in any one of the Assignee's applications listed and titled as follows:

U.S. Provisional Application Ser. No. 61/195,404 entitled "A PROCESS TO SELECTIVELY MANUFACTURE DIETHYLENETRIAMINE (DETA) AND OTHER DESIRABLE ETHYLENEAMINES VIA CONTINUOUS TRANSAMINATION OF ETHYLENEDIAMINE (EDA), AND OTHER ETHYLENEAMINES OVER A HETEROGENEOUS CATALYST SYSTEM", filed Oct. 6, 2008, in the names of Petraitis et al.;

U.S. Provisional Application Ser. No. 61/195,405 entitled "METHODS FOR MAKING ETHANOLAMINE(S) AND ETHYLENEAMINE(S) FROM ETHYLENE OXIDE AND AMMONIA, AND RELATED METHODS", filed Oct. 6, 2008, in the names of David Do et al;

U.S. Provisional Application Ser. No. 61/195,412 entitled "METHODS OF MAKING CYCLIC, N-AMINO FUNCTIONAL TRIAMINES", filed Oct. 6, 2008, in the name of Stephen W. King; and U.S. Provisional Application Ser. No. 61/61/195,454 entitled "METHOD OF MANUFACTURING ETHYLENEAMINES", filed Oct. 6, 2008, in the names of Petraitis et al.

Further, reagents and/or methods described in these co-pending applications can be incorporated by reference to further describe the use of the catalyst composition of the present invention.

Aspects of this application are related to the following Assignee's applications listed and titled as follows:

U.S. Provisional Patent Application Ser. No. 61/195,434 entitled "LOW METAL LOADED, ALUMINA SUPPORTED, CATALYST COMPOSITIONS AND AMINATION PROCESS", filed Oct. 6, 2008, in the names of King et al.

The invention will now be described with reference to the following non-limiting Examples.

EXAMPLES

The following Examples are included for illustrative purposes only, and the scope of the invention is in no way limited to the use of the particular Ni/Re catalyst compositions set forth in the Examples or to the use of EDA as the lower aliphatic alkane derivative being aminated. Similar results can be achieved using other catalyst compositions and derivatives consistent with the scope of the invention as described herein.

Unless otherwise noted, catalyst compositions were prepared using the following generalized procedure. Precursor salts of the metals (nickel and rhenium) were dissolved in 70-80° C. water to form an impregnation solution. The final volume of the impregnation solution was adjusted to equal the adsorption volume required for the number of times that the support was impregnated, and the quantities of the precursor salts were those calculated to give the metal compositions provided in the Examples. In each case the support was impregnated to incipient wetness by the addition of the appropriate amount of impregnation solution and gently agitated until all the liquid was adsorbed. The sample was then placed in a muffle furnace and calcined in air for one hour at 340° C. or as otherwise specified in the Examples. When the support had cooled, additional impregnations were performed until all of the solution had been added. A calcination step at 340° C. was done after each impregnation.

Those skilled in the art will readily appreciate that impregnation with the impregnation solution can optionally be performed in one, two, four or more incipient wetness applications, as dictated by such variables as the solubility of the precursor sales, the porosity of the support to be impregnated, and the desired weight loading of the metal.

Prior to use, the catalyst compositions were reduced in hydrogen by ramping the temperature at 3° C./minute to 230° C., holding at this temperature for one hour, and then ramping at 3° C./minute to 340° C., and holding for 3 hours, or as otherwise specified in the Examples. The catalyst compositions were allowed to cool under hydrogen to ambient temperature, after which they were stabilized by adding a flowing stream of 1% oxygen in nitrogen until the exotherm ceased. At no time was the exotherm allowed to exceed about 70° C.

The catalyst compositions were tested as extrudates; spheres, pellets or trilobes (as specified in the Examples) in a small tubular reactor for the transamination of ethylenediamine (EDA) to diethylenetriamine (DETA), as described below.

A tubular reactor consisting of a 316-stainless steel tube having an inside diameter of 1.75 cm and an overall length of about 76 cm was used for the transamination of the ethyleneamine(s) feed. Typically, 50 grams of a catalyst composition were packed into the central portion of the tube using glass beads to fill the void spaces between the catalyst particles. Glass wool plugs were used to hold the catalyst bed in place.

In each case, the reduced and stabilized catalyst composition was activated by passing approximately 45 slph of hydrogen through the bed for approximately 18 hours at 180° C. and atmospheric pressure. The reactor system was then generally brought to 600 psi and the temperature designated in the tables while still under hydrogen. A motor valve at the outlet of the reactor was used to control the system pressure.

When at the designated reaction conditions, the ethyleneamine(s) and optionally ammonia, was pumped into the reactor at an ethyleneamine(s) feed rate of approximately 15 gmole/kg cat/hr. Prior to passing through a preheater, hydrogen was introduced into the ethyleneamine(s) stream at a flow rate of about 3 slph. After passing through the preheater, which was maintained at reactor temperature, the mixture was passed into the reactor over the catalyst bed composition via upward flow. Downstream of the pressure-control valve, the reaction mixture was passed into a receiver where the product was collected in a semi-batch fashion. The liquid product was condensed in the receiver at ambient temperature, allowing the ammonia and hydrogen to flash off. The condensed sample was then analyzed by capillary gas chromatography. Each catalyst composition was tested over a temperature range of 130-210° C. to determine the effect of conversion on selectivity.

Each catalyst composition was typically tested at three to seven different temperatures, over the range of 145°-175° C., to determine the effects of conversion on selectivity. The conversion and selectivity data thus obtained were subjected to curve fitting, and the resultant equation used to calculate selectivities at 25% EDA conversion. These 25% conversion values are used in Examples 1 and 2 for purposes of catalyst selectivity comparisons at the same EDA conversion. Pressure and the EDA, NH₃ and hydrogen feed rates were held constant throughout.

The temperature required for 25% EDA conversion was determined for each catalyst. The data illustrates that the process in accordance with aspects of the invention yields an amine composition with DETA/PIP ratios as high as 14.20.

Example 1

In each of Examples 1A-1U, catalyst compositions containing 6.8 weight percent Ni, 1.8 weight percent Re on alumina-silica supports were used for the transamination of EDA to DETA. For Examples 1W, the catalyst composition included 6.8 weight percent Ni and 0.9 weight percent Re on an alumina-silica supports. For Example 1X, the catalyst composition included 6.8 weight percent Ni and 0.5 Re on an alumina-silica support. The catalysts had varying support compositions, surface areas, shapes and diameter sizes, as noted in Table 2. The catalyst compositions were tested in the tubular reactor by the above described method.

The results, shown in Table 2, demonstrate that catalyst compositions according to some aspects of the present invention can provide both high activities and high DETA selectivities. The data demonstrate that Ni/Re on an acidic mixed metal oxide (e.g., transitional alumina/silica) support can be a preferred catalyst composition for selectivity to DETA (represented as the ratio of DETA/PIP) via a transamination reaction. In addition, the data illustrate that addition of boron to the catalyst composition can have a negative impact on DETA selectivity (see Example 1V). Further, the data show using a 1/16" support versus a 1/8" support (see Example 1A and Example 1U) can improve selectivity (represented as the ratio of DETA/PIP). Also the use of a 1/16" trilobe (Example S) gave the best selectivity (DETA/PIP). These results may be due to minimizing diffusional resistances.

Comparative Example 2

Catalyst compositions 2A, 2H, and 2I were prepared in accordance with the methods described in Example 1, in accordance with some aspects of the invention.

Examples 2B through 2G were obtained from commercial sources for comparative purposes. As indicated in the Table 3, Example 2B was Raney Ni, and Examples 2C-2G included high Ni or high Co catalysts on various supports. The support of Example 2H included gamma alumina/silica support, provided as a 1/8" extrudate. The support of Example 2I included a non-transitional state alumina (silica/alumina) as part of the support, in the form of a 1/16" extrudate. As shown in Table 3, results demonstrate that activities (EDA conversion) and DETA selectivities (DETA:PIP) for the comparative samples were inferior to those obtained with Example 2A (which was prepared in accordance with aspects of the invention). Improved selectivity was observed with lower metal supports prepared in accordance with the invention, as compared to commercially obtained Example 2B-2G.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated. The patents, patent documents and publications cited herein are provided solely for their disclosure prior to the filing date of the present application. Nothing herein is to be construed as an admission that the inventor is not entitled to antedate such disclosure by virtue of prior invention.

TABLE 2

| Example | Metals | Carrier | Carrier SA (m²/g) | Temp, °C. | % Sel to DETA | DETA/PIP |
|---|---|---|---|---|---|---|
| 1A | Ni/Re (6.8/1.8 wt. %) | alumina (theta)/silica (80:20) 1/16" extrudate | 151 | 134 | 69.50 | 12.41 |
| 1B | Ni/Re (6.8/1.8 wt. %) | gamma alumina 1/8" extrudate | 250 | 159 | 66.21 | 6.48 |
| 1C | Ni/Re (6.8/1.8 wt. %) | theta alumina 1/16" extrudate | 127 | 160 | 67.15 | 9.36 |
| 1D | Ni/Re (6.8/1.8 wt. %) | gamma alumina 1/16" trilobe extrudate | 250 | 158 | 65.99 | 6.39 |
| 1E | Ni/Re (6.8/1.8 wt. %) | gamma alumina 1/16" sphere | 160 | 161 | 68.60 | 9.16 |
| 1F | Ni/Re (6.8/1.8 wt. %) | transitional alumina 1/8" trilobe extrudate | 145 | 159 | 65.48 | 7.29 |
| 1G | Ni/Re (6.8/1.8 wt. %) | transitional alumina 1/8" pellet | 145 | 157 | 68.29 | 9.91 |
| 1H | Ni/Re (6.8/1.8 wt. %) | transitional alumina 1/16" sphere | 120 | 160 | 66.45 | 9.02 |
| 1I | Ni/Re (6.8/1.8 wt. %) | transitional alumina 1/16" trilobe extrudate | 80 | 159 | 67.37 | 10.36 |
| 1J | Ni/Re (6.8/1.8 wt. %) | alumina (gamma)/silica (90:10) 1/8" CDS extr | 245 | 165 | 58.61 | 3.35 |
| 1K | Ni/Re (6.8/1.8 wt. %) | alumina (delta)/silica (90:10) 1/8" CDS extr | 134 | 151 | 68.31 | 9.88 |
| 1L | Ni/Re (6.8/1.8 wt. %) | high purity silica 1/16" extrudate | 140 | 147 | 65.10 | 6.90 |
| 1M | Ni/Re (6.8/1.8 wt. %) | silica/alumina (98:2) 1/16" extrudate | 68 | 148 | 66.91 | 8.16 |
| 1N | Ni/Re (6.8/1.8 wt. %) | gamma alumina 1/8" extrudate | 250 | 159 | 66.21 | 6.48 |
| 1O | Ni/Re (6.8/1.8 wt. %) | high purity zirconia 1/16" extrudate | 98 | 175 | 60.58 | 4.60 |
| 1P | Ni/Re (6.8/1.8 wt. %) | titania 1/16" extrudate | 45 | 170 | 64.91 | 8.18 |
| 1Q | Ni/Re (6.8/1.8 wt. %) | delta/theta mixed alumina 1.6 mm sphere | 77 | 162 | 66.86 | 9.64 |
| 1R | Ni/Re (6.8/1.8 wt. %) | delta/theta mixed alumina with 1.2% La2O3 | 103 | 162 | 66.77 | 8.49 |
| 1S | Ni/Re (6.8/1.8 wt. %) | alumina (delta/theta)silica (70:30) 1/16" trilobe | 90 | 144 | 69.30 | 14.20 |
| 1T | Ni/Re (6.8/1.8 wt. %) | alumina (theta)/silica (80:20) 1/8" extrudate | 107 | 136 | 67.09 | 10.48 |
| 1U | Ni/Re (6.8/1.8 wt. %) | alumina (theta)/silica (80:20) 1/8" extrudate | 149 | 140 | 70.11 | 11.85 |
| 1V | Ni/Re/B (8.0/2.1/1.7 wt. %) | alumina (theta)/silica (80:20) 1/8" extrudate | 107 | 148 | 68.06 | 8.76 |
| 1W | Ni/Re (6.8/0.9 wt. %) | alumina (theta)/silica (80:20) 1/8" extrudate | 107 | 146 | 68.34 | 11.63 |
| 1X | Ni/Re (6.8/0.5 wt. %) | alumina (theta)/silica (80:20) 1/8" extrudate | 107 | 150 | 66.65 | 7.84 |
| 1Y | Ni/Re (6.8/1.8 wt. %) | alumina (theta)/silica (50:50) 1/8" extrudate | 147 | 144 | 69.97 | 11.21 |
| 1Z | Ni/Re (6.8/1.8 wt. %) | zirconia/silica (75:25) 1/16" extrudate | 130 | 147 | 68.44 | 9.26 |

TABLE 3

| Example | Metals | Carrier | Temp, °C | % Sel to DETA | DETA/PIP |
|---|---|---|---|---|---|
| 2A | Ni/Re (6.8/1.8 wt. %) | alumina (theta)/silica (80:20) 1/16" extrudate | 134 | 69.50 | 12.41 |
| 2B | Ni (50 wt. %) | Grace-Davison Raney Ni 5886 fixed bed, Ni—Al 8-12 mesh | 186 | 57.70 | 5.33 |
| 2C | Ni (50 wt. %) | Sud-Chemie C46-8-03 Ni on alumina, 1/16" trilobe | 147 | 67.03 | 9.40 |
| 2D | Ni (48 wt. %) | Engelhard Ni-0750-E, Ni on gamma Alumina, 1/8" extrudate | 144 | 63.82 | 5.92 |
| 2E | Co/Zr (54/2 wt. %) | Sud-Chemie G-67 on Kieselguhr, 1/8" extrudate | 138 | 61.17 | 5.16 |
| 2F | Co (14.5 wt. %) | DeGussa 14.5% Co on gamma alumina 1 mm extrudate | 148 | 66.19 | 8.26 |
| 2G | Ni (50 wt. %) | Sud-Chemie C46-7-03, Ni on silica-alumina (2:1), 1/16" trilobe | 137 | 66.88 | 10.17 |
| 2H | Ni/Re (6.8/1.8 wt. %) | alumina (gamma)/silica (90:10) 1/8" CDS extr | 165 | 58.61 | 3.35 |
| 2I | Ni/Re (6.8/1.8 wt. %) | silica/alumina (98:2) 1/16" extrudate | 148 | 66.91 | 8.16 |

What is claimed:

1. A catalyst composition comprising:
   (a) a support portion comprising an acidic mixed metal oxide comprising a transitional alumina and a second metal oxide, wherein the second metal oxide has a weight percentage that is less than the weight percentage of alumina; and
   (b) a catalyst portion comprising nickel and rhenium, wherein:
   the catalyst portion is deposited as a shell structure on the support portion in a manner effective to provide a localized concentration of nickel and rhenium on an outer surface of the catalyst composition,
   the catalyst portion is 25 weight percent or less of the catalyst composition,
   the catalyst portion comprises nickel in an amount in the range of 2 to 20 weight percent, based upon total catalyst composition weight, and
   wherein boron constitutes less than 1 weight percent of the catalyst portion.

2. The catalyst composition according to claim 1, wherein the transitional alumina comprises delta alumina.

3. The catalyst composition according to claim 2, wherein the transitional alumina further comprises one or more of gamma, theta or alpha alumina.

4. The catalyst composition according to claim 1, wherein the transitional alumina comprises theta alumina.

5. The catalyst composition according to claim 4, wherein the transitional alumina may optionally further comprise one or more of gamma or alpha alumina.

6. The catalyst composition according to claim 1, wherein the second metal oxide comprises at least one oxide selected from the group consisting of an oxide of silicon, lanthanum, magnesium, zirconium, boron, titanium, niobium, tungsten and cerium.

7. The catalyst composition according to claim 6, wherein the second metal oxide comprises silicon.

8. The catalyst composition according to claim 1, wherein the support portion comprises the second metal oxide in an amount in the range of 5 weight percent to less than 50 weight percent, based upon the weight of the support portion.

9. The catalyst composition according to claim 1, wherein the support portion is an extrudate having an elongate morphology diameter of 1/8 inches (3.175 mm) or less.

10. The catalyst composition according to claim 1, wherein the support portion is a sphere having a diameter of 3 mm or less.

11. The catalyst composition according to claim 1, wherein the support portion is a trilobe having a diameter of 1/8 inches (3.175 mm) or less.

12. The catalyst composition according to claim 1, wherein the catalyst portion is 20 weight percent or less of the catalyst composition.

13. The catalyst composition according to claim 1, wherein the nickel and rhenium are present in the catalyst portion in a weight ratio in the range of 3:1 to 14:1.

14. The catalyst composition according to claim 1, wherein the composition further comprises a selectivity promoter that is present at a promoter/nickel weight ratio of 0.5:1 or less.

15. The catalyst composition according to claim 1, wherein the catalyst composition is an extrudate with an elongate morphology and has a diameter in the range from 0.8 mm to 3.1 mm.

16. The catalyst composition according to claim 1, wherein there is no boron in the catalyst portion.

* * * * *